US 8,663,287 B2

(12) United States Patent
Butler et al.

(10) Patent No.: US 8,663,287 B2
(45) Date of Patent: Mar. 4, 2014

(54) PEDICLE SCREW CONSTRUCTS AND SPINAL ROD ATTACHMENT ASSEMBLIES

(75) Inventors: Michael S. Butler, St. Charles, IL (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 1362 days.

(21) Appl. No.: 11/651,721

(22) Filed: Jan. 10, 2007

(65) Prior Publication Data

US 2007/0173833 A1    Jul. 26, 2007

Related U.S. Application Data

(60) Provisional application No. 60/757,660, filed on Jan. 10, 2006.

(51) Int. Cl.
*A61B 17/70* (2006.01)

(52) U.S. Cl.
USPC ............................................ 606/264; 606/267

(58) Field of Classification Search
USPC ......... 606/264, 154, 270, 272, 276, 277, 246, 606/265–269, 274, 300, 301, 305–308, 328
See application file for complete search history.

(56) References Cited

U.S. PATENT DOCUMENTS

| | | |
|---|---|---|
| 2,414,882 A | 1/1947 | Longfellow |
| 4,399,814 A | 8/1983 | Pratt, Jr. et al. |
| 4,648,388 A | 3/1987 | Steffee |

(Continued)

FOREIGN PATENT DOCUMENTS

| | | |
|---|---|---|
| WO | WO 02/36026 | 5/2002 |
| WO | WO 03/028538 | 4/2003 |
| WO | WO 2005/122965 | 12/2005 |

OTHER PUBLICATIONS

PCT International Search Report relating to International Application No. PCT/US07/00602, date of mailing of the International Search Report, Oct. 19, 2007 (3 pgs.).

(Continued)

*Primary Examiner* — Jerry Cumberledge
(74) *Attorney, Agent, or Firm* — Foley & Lardner LLP

(57) ABSTRACT

Spine fixation constructs are configured to receive and retain a spinal rod onto a vertebral bone screw. The spine fixation constructs provide for 360° rotation about a bone screw and variable axial placement about the bone screw. In one form, a rod holder of the spine fixation construct is configured to be axially received onto the bone screw. Axial positioning of the rod holder on the bone screw is fixed through cooperation of the rod holder with a fixation component. The fixation component is axially received onto the bone screw. Retention of the spinal rod by the spinal rod holder is also provided via the fixation member. In one form, spinal rod retention is provided upon axial retention of the spinal rod holder onto the bone screw through cooperating action between the fixation mechanism and the spinal rod holder. According to an embodiment, a member of the rod holder is caused to pivot and capture the spinal rod upon receipt of the fixation member onto the bone screw and rod holder. According to another embodiment, pivoting motion of a pawl of the rod holder by the fixation member not only locks the spinal rod but skews the pawl relative to the bone screw to wedge the axial placement of the pawl and thus the rod holder relative to the bone screw.

21 Claims, 16 Drawing Sheets

(56) References Cited

U.S. PATENT DOCUMENTS

| | | | |
|---|---|---|---|
| 4,653,489 A | 3/1987 | Tronzo | |
| 4,790,297 A | 12/1988 | Luque | |
| 4,805,602 A | 2/1989 | Puno et al. | |
| 4,863,472 A | 9/1989 | Tormala et al. | |
| 5,047,029 A | 9/1991 | Aebi et al. | |
| 5,092,893 A | 3/1992 | Smith | |
| 5,098,435 A | 3/1992 | Stednitz et al. | |
| 5,129,899 A | 7/1992 | Small et al. | |
| 5,261,909 A | 11/1993 | Sutterlin et al. | |
| 5,350,380 A | 9/1994 | Goble et al. | |
| 5,352,226 A | 10/1994 | Lin | |
| 5,423,819 A | 6/1995 | Small et al. | |
| 5,449,257 A | 9/1995 | Giannuzzi | |
| 5,499,983 A * | 3/1996 | Hughes | 606/267 |
| 5,545,163 A | 8/1996 | Miller | |
| 5,562,661 A | 10/1996 | Yoshimi et al. | |
| 5,569,252 A | 10/1996 | Justin et al. | |
| 5,582,612 A | 12/1996 | Lin | |
| 5,584,831 A * | 12/1996 | McKay | 606/86 A |
| 5,584,833 A | 12/1996 | Fournet-Fayard et al. | |
| 5,611,800 A | 3/1997 | Davis et al. | |
| 5,616,142 A | 4/1997 | Yuan et al. | |
| 5,643,262 A | 7/1997 | Metz-Stavenhagen et al. | |
| 5,649,931 A | 7/1997 | Bryant et al. | |
| 5,667,513 A | 9/1997 | Torrie et al. | |
| 5,688,275 A | 11/1997 | Koros et al. | |
| 5,713,900 A * | 2/1998 | Benzel et al. | 606/250 |
| 5,885,285 A * | 3/1999 | Simonson | 606/278 |
| 5,938,663 A | 8/1999 | Petreto | |
| 5,947,967 A | 9/1999 | Barker | |
| 5,951,558 A | 9/1999 | Fiz | |
| 5,976,135 A | 11/1999 | Sherman et al. | |
| 6,001,098 A | 12/1999 | Metz-Stavenhagen et al. | |
| 6,027,533 A * | 2/2000 | Olerud | 623/16.11 |
| 6,030,388 A | 2/2000 | Yoshimi et al. | |
| 6,033,406 A | 3/2000 | Mathews | |
| 6,045,555 A | 4/2000 | Smith et al. | |
| 6,048,343 A | 4/2000 | Mathis et al. | |
| 6,059,785 A | 5/2000 | Schavan et al. | |
| 6,063,089 A | 5/2000 | Errico et al. | |
| 6,063,090 A | 5/2000 | Schlapfer | |
| 6,086,588 A * | 7/2000 | Ameil et al. | 606/266 |
| 6,096,060 A | 8/2000 | Fitts et al. | |
| 6,111,164 A | 8/2000 | Rainey et al. | |
| 6,123,706 A * | 9/2000 | Lange | 606/264 |
| 6,139,549 A | 10/2000 | Keller | |
| 6,159,210 A | 12/2000 | Voor | |
| 6,179,838 B1 * | 1/2001 | Fiz | 606/278 |
| 6,183,473 B1 | 2/2001 | Ashman | |
| 6,193,721 B1 | 2/2001 | Michelson | |
| 6,210,376 B1 | 4/2001 | Grayson | |
| 6,210,413 B1 | 4/2001 | Justis et al. | |
| 6,224,602 B1 | 5/2001 | Hayes | |
| 6,228,085 B1 | 5/2001 | Theken et al. | |
| 6,231,575 B1 | 5/2001 | Krag | |
| 6,248,104 B1 | 6/2001 | Chopin et al. | |
| 6,248,105 B1 | 6/2001 | Schlapfer et al. | |
| 6,248,107 B1 | 6/2001 | Foley et al. | |
| 6,254,602 B1 | 7/2001 | Justis | |
| 6,258,089 B1 | 7/2001 | Campbell et al. | |
| 6,273,889 B1 | 8/2001 | Richelsoph | |
| 6,306,136 B1 | 10/2001 | Baccelli | |
| 6,315,779 B1 | 11/2001 | Morrison et al. | |
| 6,317,957 B1 | 11/2001 | Gregor et al. | |
| 6,355,039 B1 | 3/2002 | Troussel et al. | |
| 6,364,881 B1 | 4/2002 | Apgar et al. | |
| 6,371,957 B1 | 4/2002 | Amrein et al. | |
| 6,379,357 B1 | 4/2002 | Bernstein et al. | |
| 6,398,783 B1 | 6/2002 | Michelson | |
| 6,402,749 B1 | 6/2002 | Ashman | |
| 6,402,756 B1 | 6/2002 | Ralph et al. | |
| 6,413,259 B1 | 7/2002 | Lyons et al. | |
| 6,428,542 B1 | 8/2002 | Michelson | |
| 6,454,769 B2 | 9/2002 | Wagner et al. | |
| 6,471,703 B1 | 10/2002 | Ashman | |
| 6,503,250 B2 | 1/2003 | Paul | |
| 6,533,786 B1 | 3/2003 | Needham et al. | |
| 6,547,789 B1 * | 4/2003 | Ventre et al. | 606/308 |
| 6,582,436 B2 * | 6/2003 | Schlapfer et al. | 606/266 |
| 6,599,290 B2 | 7/2003 | Bailey et al. | |
| 6,602,257 B1 | 8/2003 | Thramann | |
| 6,613,050 B1 | 9/2003 | Wagner et al. | |
| 6,616,665 B2 | 9/2003 | Grafton et al. | |
| 6,620,163 B1 | 9/2003 | Michelson | |
| 6,626,906 B1 | 9/2003 | Young | |
| 6,641,583 B2 | 11/2003 | Shulzas et al. | |
| 6,641,586 B2 | 11/2003 | Varieur | |
| 6,648,887 B2 | 11/2003 | Ashman | |
| 6,648,894 B2 | 11/2003 | Abdelgany et al. | |
| 6,663,642 B2 | 12/2003 | Beyar et al. | |
| 6,668,688 B2 | 12/2003 | Zhao et al. | |
| 6,669,700 B1 | 12/2003 | Farris et al. | |
| 6,676,661 B1 | 1/2004 | Martin Benlloch et al. | |
| 6,685,705 B1 | 2/2004 | Taylor | |
| 6,695,846 B2 | 2/2004 | Richelsoph et al. | |
| 6,706,045 B2 | 3/2004 | Lin et al. | |
| 6,723,100 B2 | 4/2004 | Biedermann et al. | |
| 6,749,613 B1 * | 6/2004 | Conchy et al. | 606/57 |
| 6,755,835 B2 | 6/2004 | Schultheiss et al. | |
| 6,786,907 B2 * | 9/2004 | Lange | 606/250 |
| 6,827,722 B1 | 12/2004 | Schoenefeld | |
| 6,832,999 B2 | 12/2004 | Ueyama et al. | |
| 6,835,196 B2 | 12/2004 | Biedermann et al. | |
| 6,858,030 B2 | 2/2005 | Martin et al. | |
| 6,887,197 B2 * | 5/2005 | Phillips | 600/213 |
| 6,893,444 B2 | 5/2005 | Orbay | |
| 6,899,714 B2 | 5/2005 | Vaughan | |
| 6,949,100 B1 | 9/2005 | Venturini | |
| 6,951,561 B2 | 10/2005 | Warren et al. | |
| 6,960,212 B2 * | 11/2005 | Richelsoph et al. | 403/342 |
| 7,104,992 B2 | 9/2006 | Bailey | |
| 7,591,838 B2 * | 9/2009 | Kramer et al. | 606/265 |
| 7,594,924 B2 * | 9/2009 | Albert et al. | 606/267 |
| 7,744,632 B2 | 6/2010 | Usher | |
| 7,744,635 B2 | 6/2010 | Sweeney et al. | |
| 7,938,848 B2 | 5/2011 | Sweeney | |
| 8,021,398 B2 | 9/2011 | Sweeney et al. | |
| 8,066,746 B2 | 11/2011 | Glerum et al. | |
| 8,070,781 B2 | 12/2011 | Harper | |
| 2001/0041894 A1 | 11/2001 | Campbell et al. | |
| 2002/0045896 A1 | 4/2002 | Michelson | |
| 2002/0045899 A1 | 4/2002 | Errico et al. | |
| 2002/0111630 A1 | 8/2002 | Ralph et al. | |
| 2002/0120273 A1 | 8/2002 | Needham et al. | |
| 2002/0128655 A1 | 9/2002 | Michelson | |
| 2002/0143332 A1 | 10/2002 | Lin et al. | |
| 2002/0143341 A1 | 10/2002 | Biedermann et al. | |
| 2002/0147450 A1 | 10/2002 | LeHuec et al. | |
| 2002/0151899 A1 | 10/2002 | Bailey et al. | |
| 2002/0169450 A1 * | 11/2002 | Lange | 606/61 |
| 2002/0183748 A1 | 12/2002 | Martin et al. | |
| 2002/0183754 A1 | 12/2002 | Michelson | |
| 2002/0183755 A1 | 12/2002 | Michelson | |
| 2002/0183756 A1 | 12/2002 | Michelson | |
| 2002/0183757 A1 | 12/2002 | Michelson | |
| 2002/0188296 A1 | 12/2002 | Michelson | |
| 2003/0000350 A1 | 1/2003 | Zhao et al. | |
| 2003/0023240 A1 | 1/2003 | Amrein et al. | |
| 2003/0023242 A1 | 1/2003 | Harrington, Jr. | |
| 2003/0040749 A1 | 2/2003 | Grabowski et al. | |
| 2003/0045878 A1 | 3/2003 | Petit et al. | |
| 2003/0060828 A1 | 3/2003 | Michelson | |
| 2003/0073997 A1 | 4/2003 | Doubler et al. | |
| 2003/0083658 A1 | 5/2003 | Hawkes et al. | |
| 2003/0105460 A1 | 6/2003 | Crandall et al. | |
| 2003/0105462 A1 | 6/2003 | Haider | |
| 2003/0149431 A1 | 8/2003 | Varieur | |
| 2003/0149432 A1 | 8/2003 | Frigg et al. | |
| 2003/0171751 A1 | 9/2003 | Ritland | |
| 2003/0191473 A1 | 10/2003 | Taylor | |
| 2003/0208202 A1 | 11/2003 | Falahee | |
| 2004/0010253 A1 | 1/2004 | Morrison | |
| 2004/0034356 A1 | 2/2004 | LeHuec et al. | |
| 2004/0068319 A1 | 4/2004 | Cordaro | |

(56) References Cited

U.S. PATENT DOCUMENTS

| | | |
|---|---|---|
| 2004/0087951 A1 | 5/2004 | Khalili |
| 2004/0092930 A1 | 5/2004 | Petit et al. |
| 2004/0102773 A1 | 5/2004 | Morrison et al. |
| 2004/0102780 A1 | 5/2004 | West, Jr. |
| 2004/0106924 A1 | 6/2004 | Ralph et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127899 A1 | 7/2004 | Konieczynski et al. |
| 2004/0138661 A1 | 7/2004 | Bailey |
| 2004/0147928 A1 | 7/2004 | Landry et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204712 A1 | 10/2004 | Kolb et al. |
| 2004/0215190 A1 | 10/2004 | Nguyen et al. |
| 2004/0220571 A1 | 11/2004 | Assaker et al. |
| 2004/0220572 A1 | 11/2004 | Michelson |
| 2004/0236335 A1 | 11/2004 | Michelson |
| 2004/0243139 A1 | 12/2004 | Lewis et al. |
| 2004/0254574 A1 | 12/2004 | Morrison et al. |
| 2005/0010216 A1* | 1/2005 | Gradel et al. ............... 606/61 |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038433 A1* | 2/2005 | Young ....................... 606/61 |
| 2005/0043732 A1 | 2/2005 | Dalton |
| 2005/0059971 A1 | 3/2005 | Michelson |
| 2005/0070901 A1 | 3/2005 | David |
| 2005/0075699 A1 | 4/2005 | Olson et al. |
| 2005/0090821 A1* | 4/2005 | Berrevoets et al. ......... 606/61 |
| 2005/0113830 A1 | 5/2005 | Rezach et al. |
| 2005/0113833 A1 | 5/2005 | Davison |
| 2005/0149026 A1 | 7/2005 | Butler et al. |
| 2005/0277923 A1 | 12/2005 | Sweeney |
| 2005/0277931 A1 | 12/2005 | Sweeney et al. |
| 2006/0079903 A1 | 4/2006 | Wong |
| 2006/0089647 A1 | 4/2006 | Culbert et al. |
| 2006/0149234 A1 | 7/2006 | de Coninck |
| 2006/0195096 A1 | 8/2006 | Lee et al. |
| 2006/0224241 A1 | 10/2006 | Butler et al. |
| 2006/0247626 A1* | 11/2006 | Taylor et al. ............... 606/61 |
| 2007/0118122 A1 | 5/2007 | Butler et al. |
| 2007/0173833 A1 | 7/2007 | Butler et al. |
| 2009/0043339 A1 | 2/2009 | Tepper et al. |
| 2009/0062860 A1 | 3/2009 | Frasier et al. |
| 2009/0093848 A1 | 4/2009 | Neary et al. |
| 2009/0099604 A1 | 4/2009 | Cho et al. |
| 2009/0131985 A1 | 5/2009 | Mazda et al. |
| 2009/0234391 A1 | 9/2009 | Butler et al. |
| 2009/0287253 A1 | 11/2009 | Felix et al. |
| 2010/0160971 A1 | 6/2010 | Glerum et al. |
| 2010/0268279 A1 | 10/2010 | Gabelberger et al. |
| 2012/0130426 A1 | 5/2012 | Thompson |
| 2012/0179204 A1 | 7/2012 | Rathbun et al. |

OTHER PUBLICATIONS

"The Trio® Spinal System," printed Feb. 9, 2005, 2 pages.
Chen, Pei-Yu et al., "Closed Reduction With Intramedullary Fixation for Midclavicular Fractures," Orthopedics Journal, May 2004, pp. 459-462, vol. 27, No. 5.
Lamendola, Mark, How to Use Belleville Washers Correctly, Dec. 1, 1997, EC&M, 2 pages.

* cited by examiner

PEDICLE SCREW CONSTRUCTS AND SPINAL ROD ATTACHMENT ASSEMBLIES

RELATED APPLICATIONS

This patent application claims the benefit of and/or priority to U.S. Provisional Patent Application No. 60/757,660 filed Jan. 10, 2006, entitled "Pedicle Screw Construct and Spinal Rod Attachment Assembly" the entire contents of which is specifically incorporated by reference.

BACKGROUND OF THE INVENTION

1. Field of the Invention

The present invention relates to spine fixation components and constructs.

2. Background Information

Pedicle screw fixation has made a profound contribution to the correction of spinal deformities in the thoracic, lumbar, and sacral spine, as well as other spinal problems. Pedicle screws are specially designed and manufactured bone screws that are placed through the pedicles of the spinal column into the vertebral body. Screws placed in this manner offer superior strength and pull-out resistance as compared to other forms of fixation in spine surgery. The ability to achieve pedicle fixation has allowed surgeons to obtain more secure fixation of the involved vertebral segments, which permits more powerful correction of spine problems and reported better clinical outcomes.

Pedicle screws provide a foundation for attaching spinal rods. A spinal rod connector is attached to a pedicle screw and holds a spinal rod relative to the pedicle screw. The pedicle screw and spinal rod connector may be considered a spine fixation construct. There are various types of spine fixation constructs. One type of spine fixation construct is known as the TSRH-3D® spine fixation construct from Medtronic Sofamor Danek. The TSRH-3D® spine fixation construct allows for inter-operative adjustments in the coronal, transverse and sagittal planes. Particularly, the TSRH-3D® construct allows for six degrees of freedom for attachment to the pedicle screws from any direction, angle, and height. Even with the flexibility offered by the TSRH-3D®, there is room for improvement.

Thus, spinal rods can be rigidly locked into a variety of configurations, along with other types of implant components. This allows a surgeon to tailor-make each construct for the individual case. In addition, some constructs allow for no in-situ threading. This decreases operative time by allowing the construct to be pre-assembled while the surgeon places the pedicle screws.

The prior art spine fixation constructs, however, lack in various respects. Therefore, there is a need for a spine fixation construct that easily receives, holds and retains a spinal rod.

SUMMARY OF THE INVENTION

The present invention provides various spine fixation constructs for receiving and retaining a spinal rod onto a vertebral bone screw. In one form, a rod holder of the spine fixation construct is configured to be axially received onto the bone screw. The axial positioning of the rod holder on the bone screw is fixed through cooperation of the rod holder with a fixation component. The fixation component is axially received onto the bone screw.

In another form, retention of the spinal rod by the spinal rod holder is provided upon axial retention of the spinal rod holder onto the bone screw through cooperating action between the fixation mechanism and the spinal rod holder.

According to an embodiment, a member of the rod holder is caused to pivot and capture the spinal rod upon receipt of the fixation member onto the bone screw and rod holder.

In, another form, pivoting motion of a pawl of the rod holder by the fixation member not only locks the spinal rod but skews the pawl relative to the bone screw to wedge the axial placement of the pawl and thus the rod holder relative to the bone screw.

According to an embodiment, there is provided a spine fixation construct for receiving and retaining a spinal rod onto a bone screw. The spine fixation construct includes a rod holder configured to be axially received and positioned onto a bone screw and to receive and lock onto a spinal rod when engaged, and a fixation component configured to be axially received on the bone screw and the rod holder, the fixation component further configured to fix the axial position of the rod holder on the bone screw and to engage the rod holder when the fixation component fixes the axial position of the rod holder on the bone screw.

According to another embodiment, there is provided a spine fixation construct including a bone screw having a threaded shank and a head, a rod holder configured to be axially received and positioned onto the head of the bone screw and to receive and lock onto a spinal rod when engaged, and a fixation device configured to be axially received on the head of the bone screw and the rod holder, the fixation device further configured to fix the axial position of the rod holder on the bone screw and to engage the rod holder when the fixation device fixes the axial position of the rod holder on the bone screw.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

Figure 1:
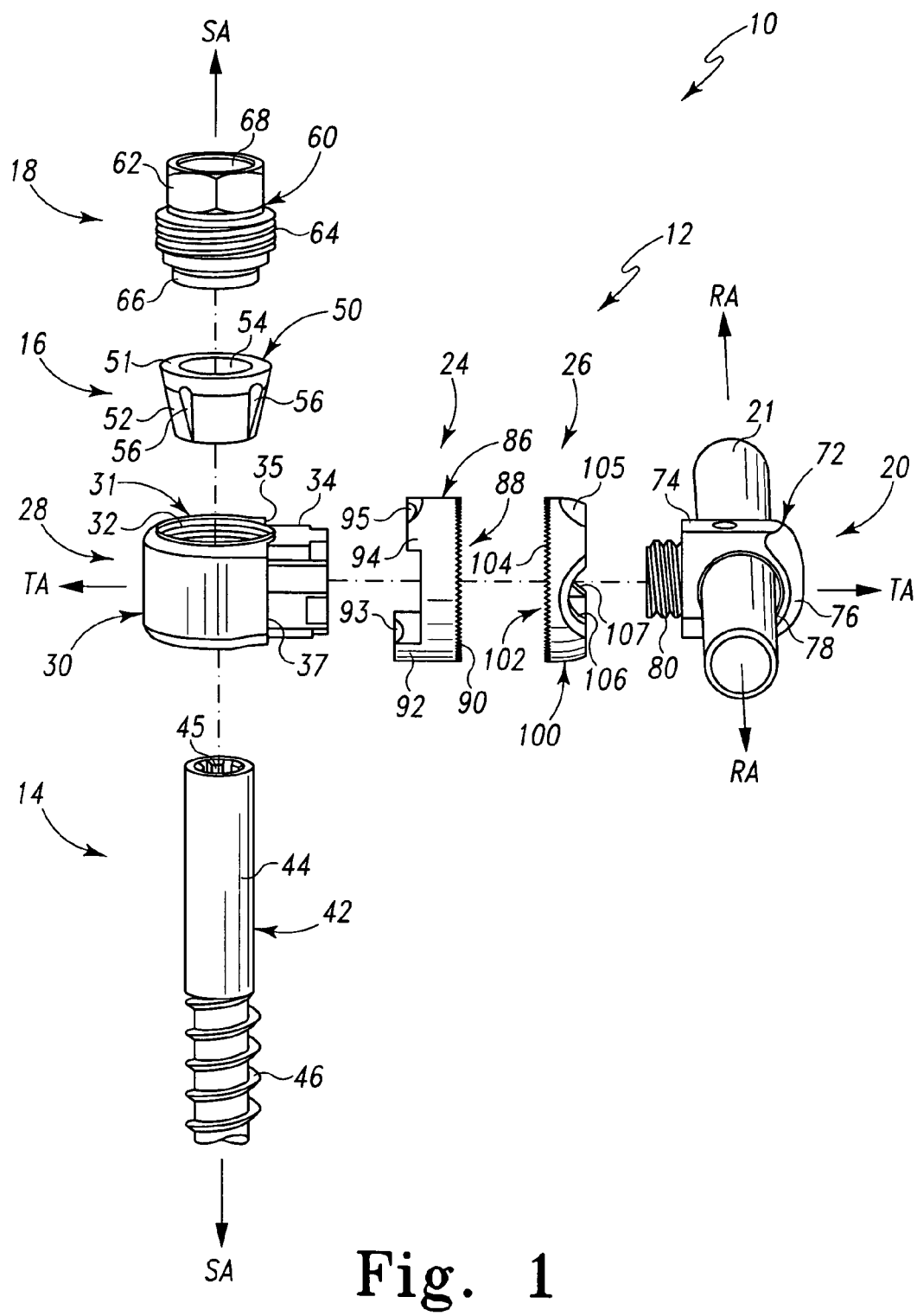
FIG. 1 is an exploded side perspective view of an exemplary embodiment of a spine fixation assembly fashioned in accordance with the present principles.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

SUMMARY OF THE INVENTION

FIGS. 1-8 depict various views of a spine fixation construct 10 for holding a spinal rod portion of a spinal rod (spinal rod) 21. The spine fixation construct 10 consists of a spinal rod holder or holding assembly 12, a bone screw 14, a collet 16 and a nut 18, the collet 16 and nut 18 providing a retention mechanism for fixing the spinal rod holder 12 onto the bone screw 14. The spinal rod holder 12 is configured and/or adapted to be retained on the bone screw 14 and to receive and retain the spinal rod 21 relative to the bone screw 14. The spinal rod holder 12 provides for variable adjustment thereof relative to the bone screw 14 and thus the variable adjustment of the spinal rod 21 relative to the bone screw 14. Such adjustment is described herein. The spine fixation construct is able to provide adjustment in the coronal, transverse and sagittal planes.

The bone screw 14 is defined by a cylindrical body or shaft 42 having a threaded lower portion 46 and a smooth upper portion 44. The screw body 42 has a configured socket 45 on the upper end thereof. The socket 45 is configured to allow the threading of the bone screw 14 into a vertebral body (bone). The bone screw 14 defines an axis (SA). The bone screw 14 is preferably, but not necessarily, a pedicle screw.

Figure 2:
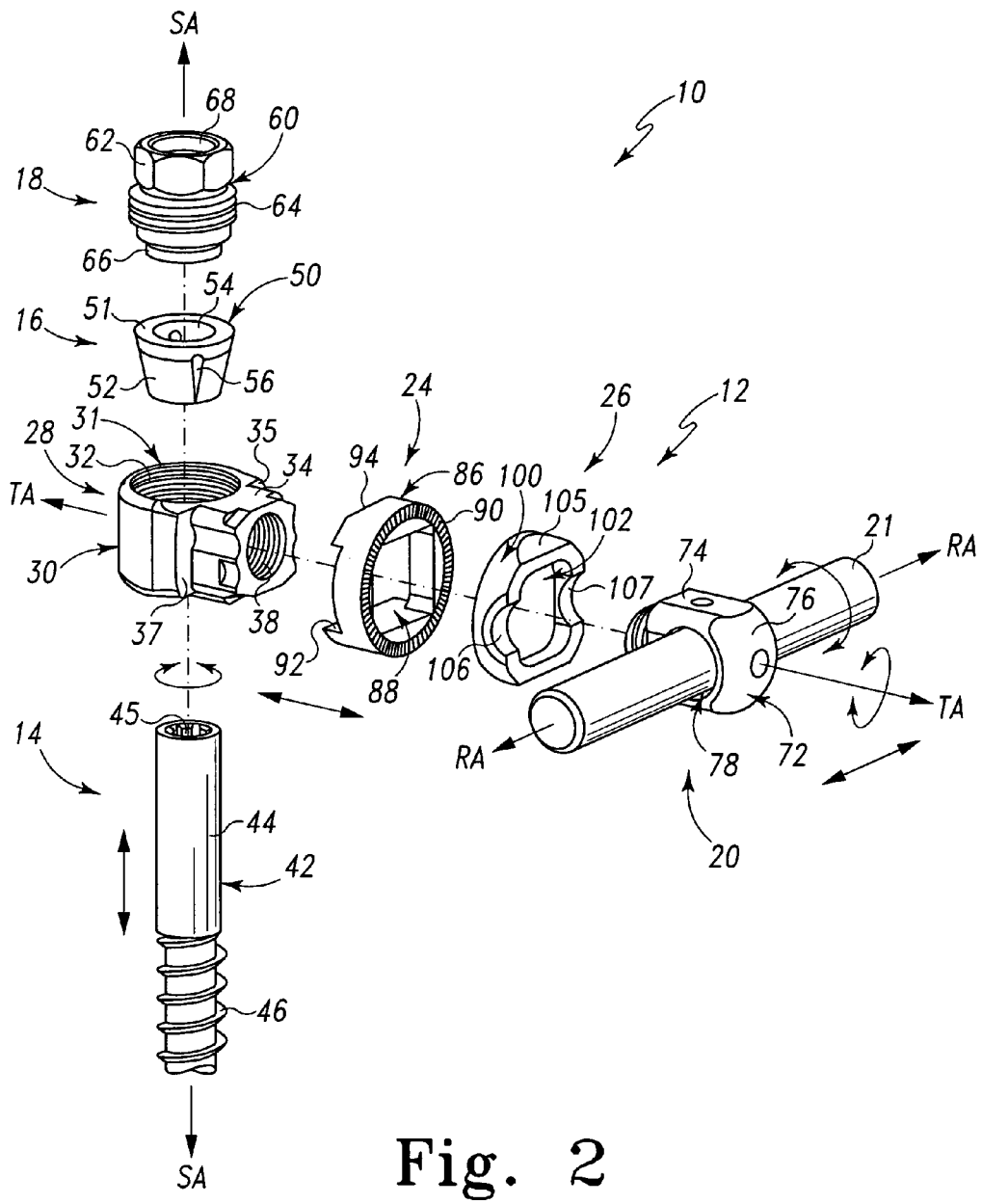
FIG. 2 is an exploded perspective view of the spine fixation assembly of FIG. 1.
Figure 3:
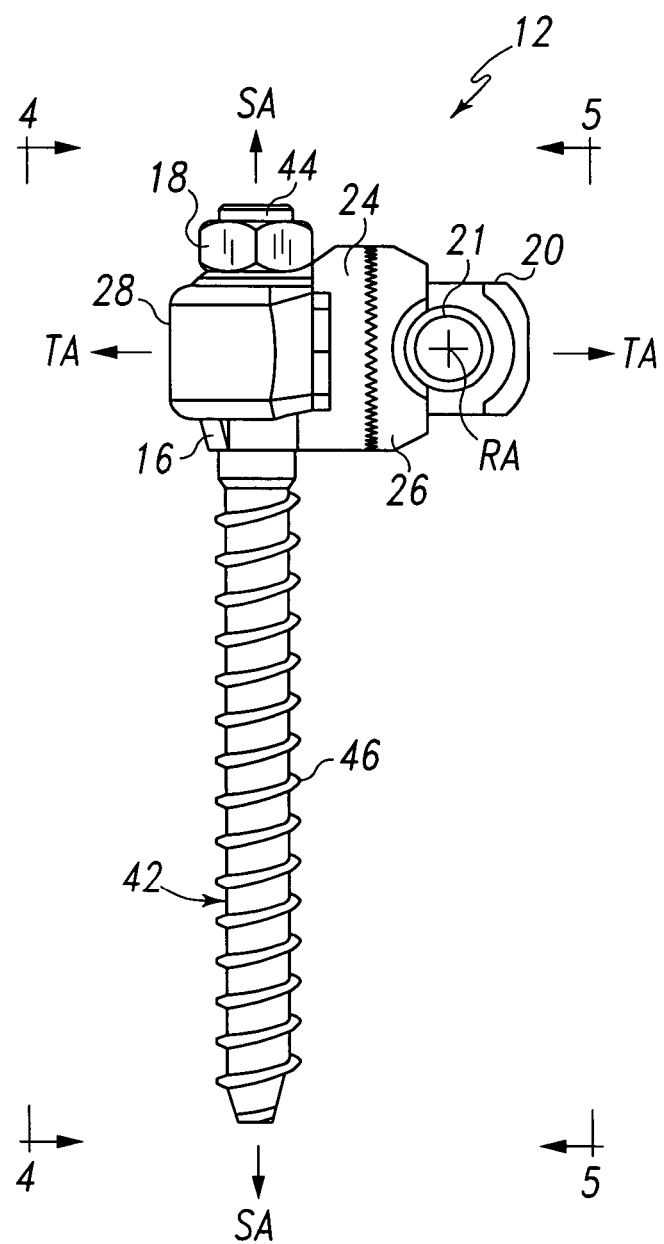
FIG. 3 is a side view of the spine fixation assembly of FIG. 1, assembled, the view of FIG. 3 taken along line 3-3 of FIG. 5.
Figure 4:
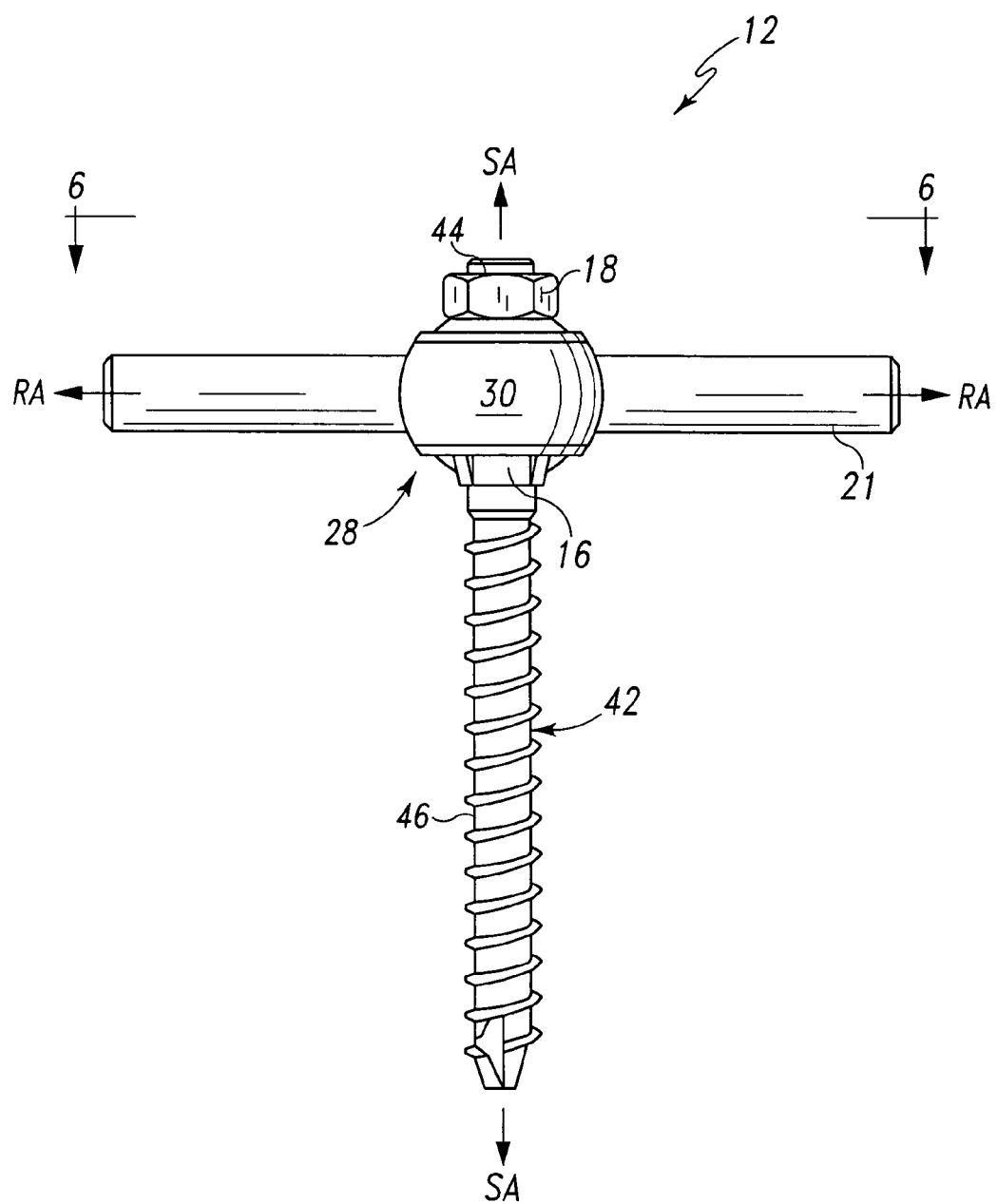
FIG. 4 is a front view of the spine fixation assembly of FIG. 1, assembled, the view of FIG. 4 taken along line 4-4 of FIG. 3.
Figure 5:
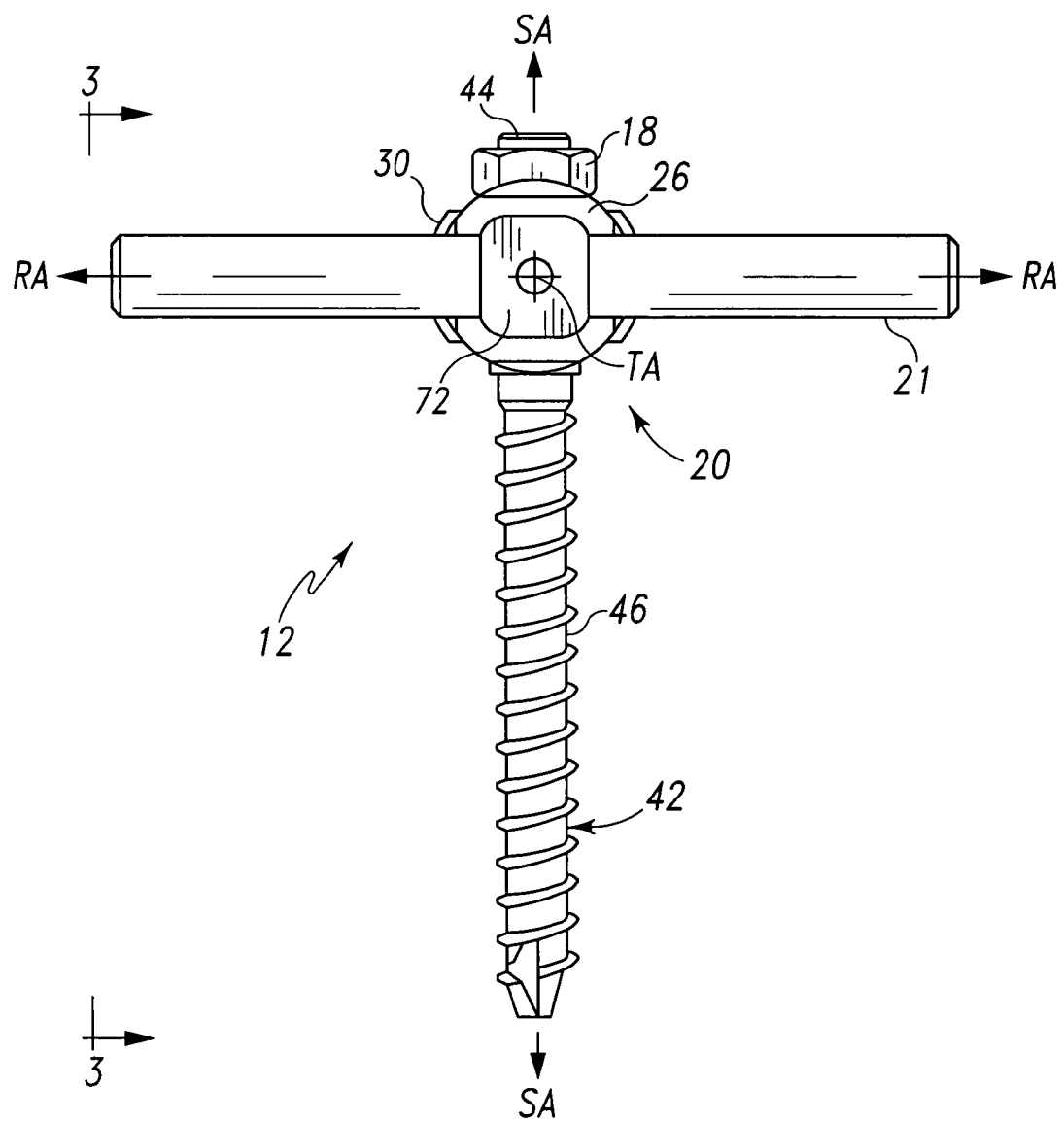
FIG. 5 is a rear view of the spine fixation assembly of FIG. 1, assembled, the view of FIG. 5 taken along line 5-5 of FIG. 3.
Figure 6:
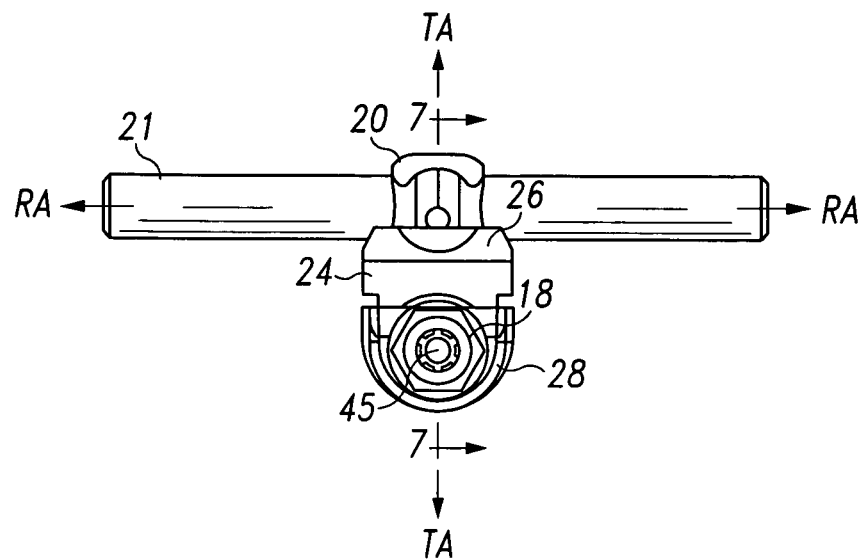
FIG. 6 is a top view of the spine fixation assembly of FIG. 1, assembled, the view of FIG. 5 taken along line 6-6 of FIG. 4.
Figure 7:
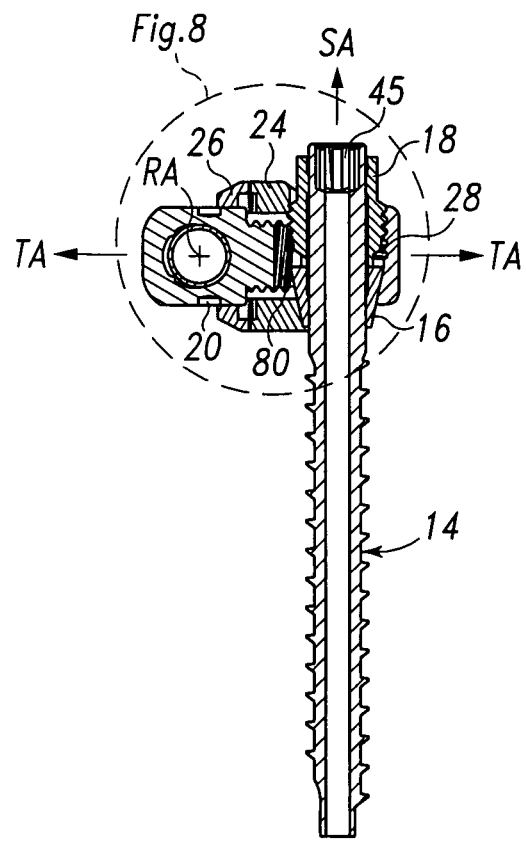
FIG. 7 is a sectional view of the spine fixation assembly of FIG. 1, assembled, the view of FIG. 7 taken along line 7-7 of FIG. 6.

The spinal rod holder 12 is defined by a rod holder 20, a sleeve 28, and first and second collars 24 and 26. The sleeve 28 is defined by a generally tubular body 30 having a bore 31 therethrough. The bore 31 has threads 32 on an upper portion thereof. The body 30 also includes a generally rectangular projection 34 extending generally perpendicular (transverse) to the bore 31. The body 30 define a flat 35 on one side of the projection 34 and another flat 37 on another side of the projection 34 opposite to the flat 35. As best seen in FIG. 2, the projection has an internally threaded bore 38.

The first collar 24 is defined by a generally ring-shaped body 86 having a generally rectangular bore 88. A toothed annulus 90 surrounds a front face of the body 86. A first flat 92 extends from a rear face of the body 86 and includes a notch 93. A second flat 94 extends from the rear face of the body 86 and includes a notch 95. The first and second flats 92, 94 are situated on the rear face of the body 86 so as to be diametrically opposed. The first and second flats 92, 94 are configured to be received over and onto the rectangular projection 34 of the sleeve 28.

The second collar 26 is defined by a generally ring-shaped body 100 having a generally rectangular bore 102. A toothed annulus 104 surrounds a rear face of the body 100. An upper flat 105 is formed on the outer surface of the body 100. A first arced portion 106 is defined in a front face of the body 100. A second arced portion 107 is also defined in the front face of the body 100. The first and second arced portions 106, 107 are situated on the front face of the body 100 so as to be diametrically opposite one another. The curvature of the first and second arced portions 106, 107 are such as to accommodate the curvature of the generally cylindrical spinal rod 21.

Figure 8:
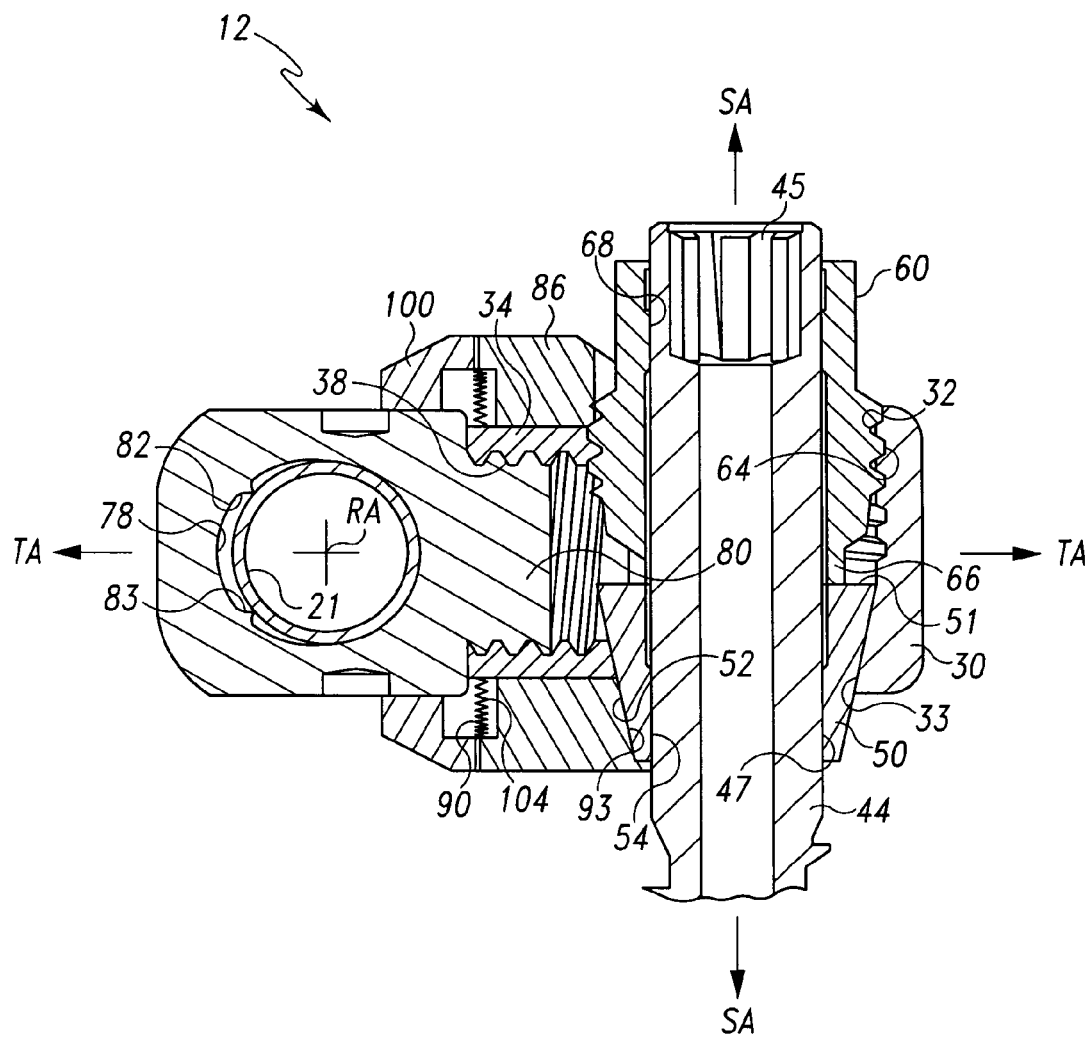
FIG. 8 is an enlarged view of a portion of the sectional view of FIG. 7 taken along circle 8-8 of FIG. 7.
Figure 9:
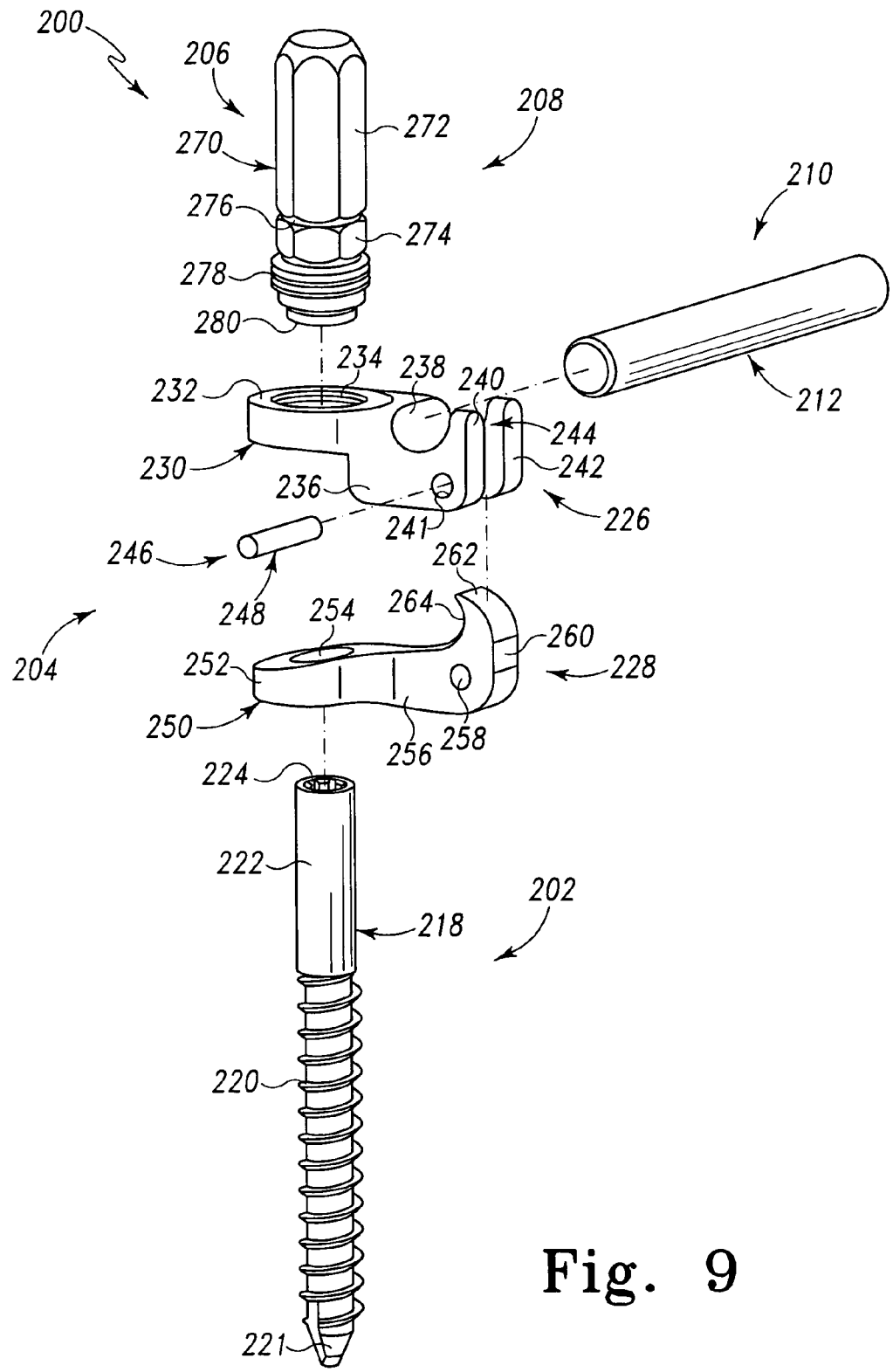
FIG. 9 is an exploded perspective view of another exemplary embodiment of a spine fixation assembly fashioned in accordance with the present principles.

The rod holder 20 is defined by a generally rectangular body 72 having a block portion 74 and a nose portion 76. The block portion 74 is sized to be received in the rectangular bores 102 and 88 of the second and first collars 26 and 24 respectively. The block portion 74 includes a bore 78 that is sized to receive the spinal rod 21, the spinal rod 21 defining an axis RA. As best seen in FIG. 8, the bore 78 is somewhat oblong or oval and includes first and second spikes or pointed projections 82 and 83. The first and second spikes 82, 83 provide a grip on the spinal rod 21. The body 72 further includes a threaded projection 80 that extends from a rear of the block portion 74. The threaded projection 80 is adapted to be threadedly received in the threaded bore 38 of the sleeve 28.

When assembled, the teeth of the toothed annulus 104 of the second collar 28 engages the teeth of the toothed annulus 90 of the first collar 24 to fix the rotational position of the second collar 28 and thus the rotational position of the spinal rod 21 relative to the screw axis SA. The spacing of the teeth of both toothed annuli 90, 104 are such as to provide for small radial increments or positions.

The sleeve 28 is axially received onto the bone screw 14 and is variably positionable up and down (axially) with respect to the bone screw 14. Particularly, the sleeve 28 is received onto the upper portion 44 of the shaft 42 of the bone screw 14. Height of the sleeve 28 is adjusted by moving the sleeve 28 up or down on the upper portion 44. Additionally, rotational position of the sleeve 28 is continuously adjustable (360°) about the bone screw 14 (bone screw axis SA) such that the projection 34 that receives the rod holder 20 may be positioned in any radial orientation relative to the bone screw 14.

The height and radial position of the sleeve 28 is fixed relative to the bone screw via the collet 16 and the nut 18. The collet 16 is defined by a body 50 that is generally a truncated cone and thus has a frustoconical outer surface 52. The body 50 has a bore 54 therethrough that defines an annular upper surface 51. The bore 54 is sized to receive the upper portion 44 of the bone screw shaft 42 therethrough. A plurality of axially extending notches 56 are provided about the frustoconical outer surface 52. The collet 16 is sized to be received in the bore 31 of the sleeve 28.

The nut 18 is defined by a body 60 that has a bore 68 therethrough that is sized to receive the upper portion 44 of the bone screw shaft 42 therethrough. The body 60 also includes a hexagonal upper portion 62, a threaded middle portion 62 and a lower annular portion 66. The threaded middle portion 62 is adapted to threadedly engage the threads 32 of the bore 31 of the sleeve 28. The manner of fixing the sleeve 28 (and thus its positions relative) to the bone screw 14 is described below with reference to FIG. 8.

Referring then to FIG. 8, a close-up of the spinal rod holder 12 as it is attached onto the bone screw 14 via the collet 16 and nut 18 is shown. Once the up/down and rotational position of the sleeve 28 is achieved, the nut 18 is threadedly engaged with the sleeve 28. During threaded engagement thereof, the end 66 of the nut 18 contacts the upper surface 51 of the collet 16. This movement forces the frustoconical outer surface 52 of the collet 16 downward for wedging engagement thereof to the inner surface 33 of the sleeve bore 32. Thus the position of the sleeve 28 is fixed. The rotational position of the spinal rod 21 and thus the rod axis (RA) relative to a perpendicular or transverse axis (TA) relative to the bone screw axis (SA) is changed by rotation of the second collar 26 relative to the first collar 24. There is 360° of rotation possible of the second collar 26 relative to the first collar 24. Threaded engagement of the rod holder 20 into the sleeve 28 retains the rod 21 into the arced notches 106, 107 of the second collar 26. In this manner, the present spinal fixation construct 10 provides adjustment in various planes.

FIGS. 9-13 depict various views of another spine fixation construct 200 for holding a spinal rod portion 212 of a spinal rod (spinal rod) 210. The spine fixation construct 200 consists of a spinal rod holder or holding assembly 204, a bone screw 202, and a fixation mechanism 206. The spinal rod holder 204 is configured and/or adapted to be retained onto the bone screw 202 and to receive and retain the spinal rod portion 212 relative to the bone screw 202. The spinal rod holder 204 is further configured to lock onto the spinal rod portion 212. This locking of the spinal rod is accomplished upon receipt of the fixation mechanism 206 onto the bone screw 202. Particularly, as the fixation mechanism 206 is received onto the bone screw 202 the fixation mechanism 206 cooperates with the spinal rod holder 204 to cause the spinal rod holder 204 to lock onto the spinal rod 212. Such cooperation also locks or fixes the axial position of the rod holder 204 on the bone screw 202. The spine fixation construct 200 provides locking of a spinal rod by the spinal rod holder 204 upon axial retention of the spinal rod holder 204 onto the bone screw 202 through cooperating action between the fixation mechanism 206 and the spinal rod holder 204. As represented by 208, a spine fixation construct may consist only of a rod holder as described herein and a fixation component as described herein.

The bone screw 202 is defined by a generally elongated cylindrical body or shaft 218 having a threaded lower portion or shank 220 tapering to an end or tip 221 and a smooth, generally cylindrical upper portion or head 222. The upper portion 222 has a configured socket 224 on the upper end thereof. The socket 224 is configured to allow receipt of a like-configured tool for threading the bone screw 218 into and out of a vertebral body, vertebrae or bone. The threaded lower portion 220 is configured to be received by the vertebral body, vertebrae or bone. The bone screw 202 is preferably, but not necessarily, configured as a pedicle screw.

The spinal rod holder or holding assembly 204 is defined by a connector 226, a rod retention or locking mechanism, latch, pawl or pivoting member 228, and a pivot pin 246. The pawl 228 is pivotally attached to the connector 226 through the pivot pin 246. The spinal rod holder 204 is configured to be received and fixed onto the bone screw 202 and particularly the upper portion 222 of the bone screw 202. The spinal rod holder 204 is further configured to receive the spinal rod 212 and lock or positively retain the spinal rod in cooperation with the fixation mechanism 206.

The connector 226 is defined by a body 230 having a generally annular portion 232 and a neck portion 236 essentially radially extending from the annular portion 232. The annular portion 232 has a threaded bore 234 that is sized to be received about the upper portion 222 of the bone screw 202. The neck portion 236 has first and second prongs or legs 240, 242 that define a slot or channel 244 therebetween. The neck portion 236 also has a rod reception area or recess 238 that is sized to receive the spinal rod 212. The first prong 240 has a bore 241 for receipt of the pivot pin 248 therethrough. The second prong 242 likewise has a bore (not seen) for receipt of the pivot pin 248 therethrough.

Figure 13:
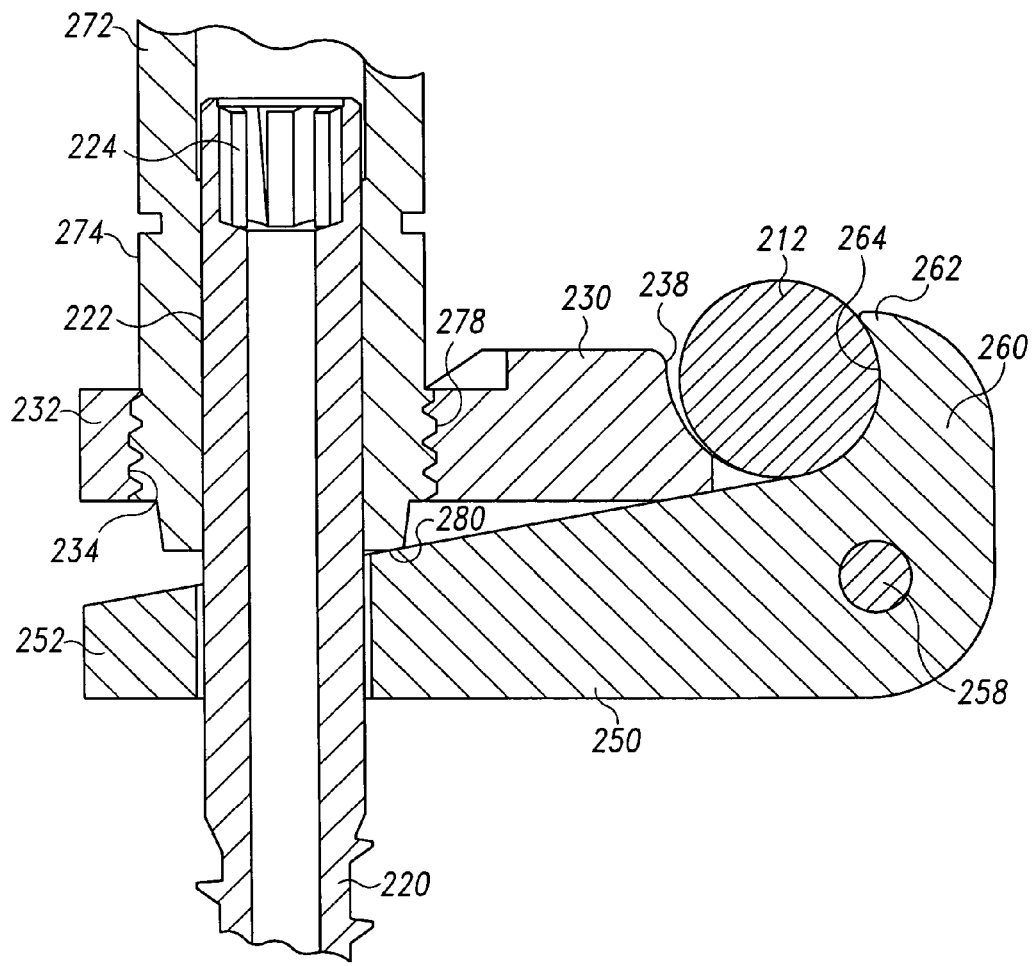
FIG. 13 is an enlarged view of a portion of the sectional view of FIG. 12 taken along circle 13-13 of FIG. 12.
Figure 14:
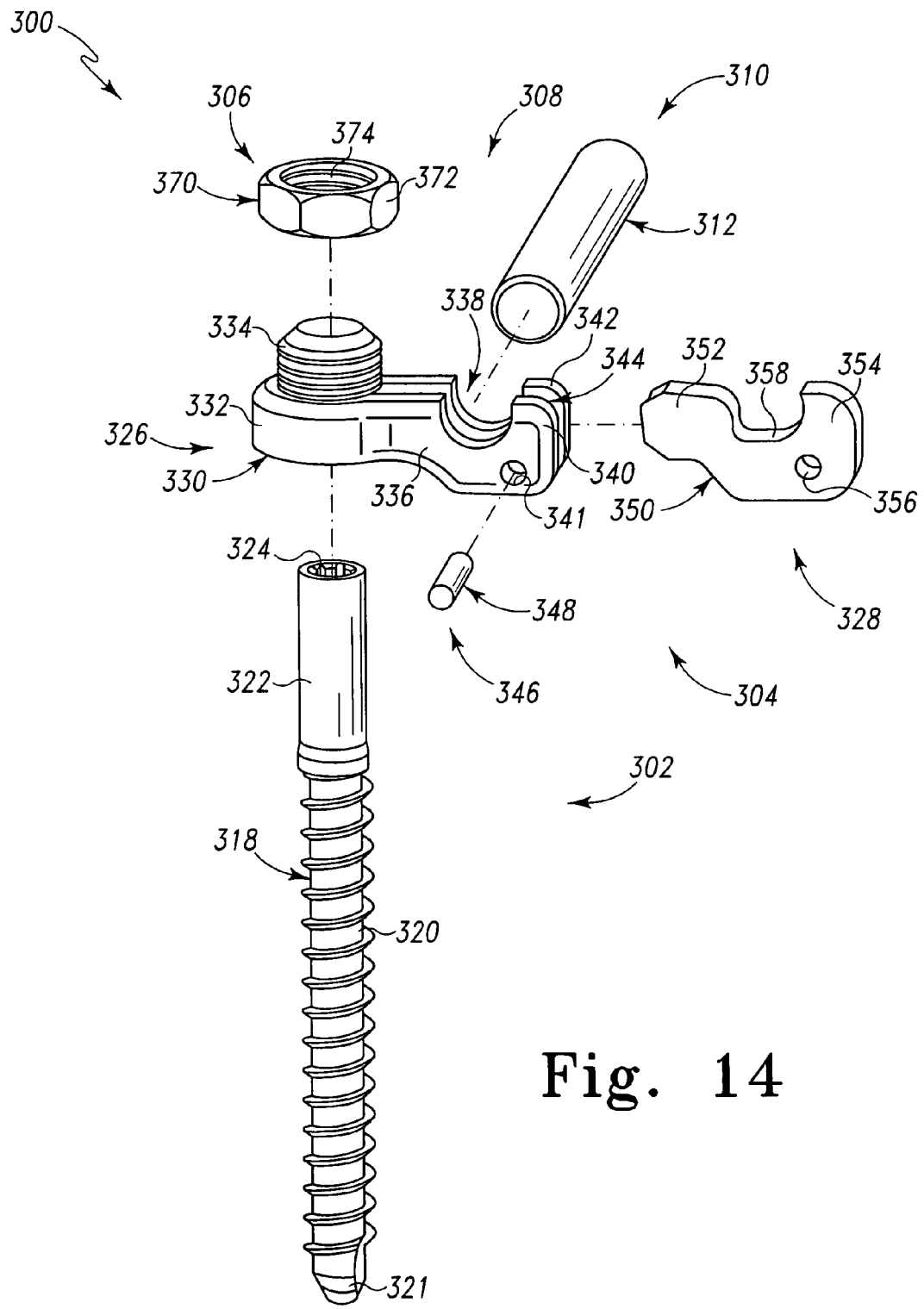
FIG. 14 is an exploded perspective view of another exemplary embodiment of a spine fixation assembly fashioned in accordance with the present principles.
Figure 15:
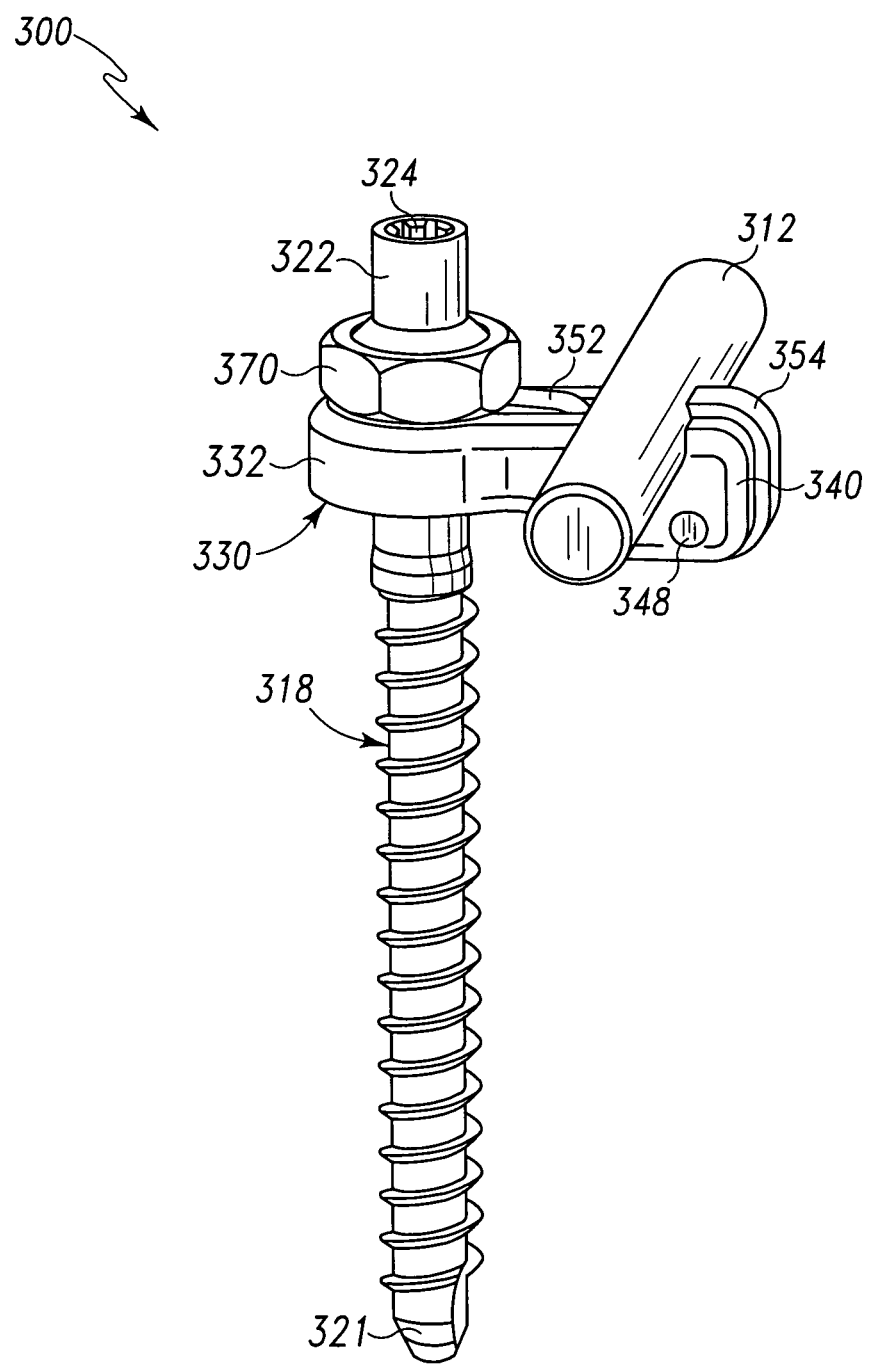
FIG. 15 is a perspective view of the spine fixation assembly of FIG. 14 assembled.
Figure 16:
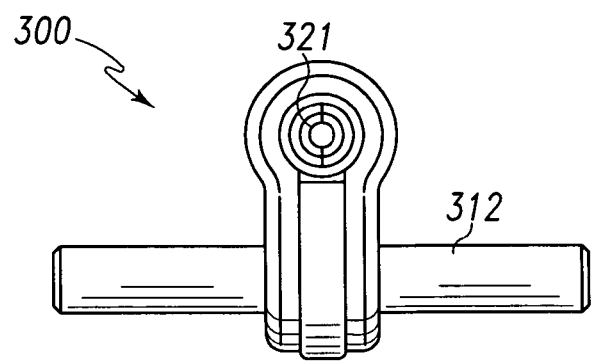
FIG. 16 is a top view of the spine fixation assembly of FIG. 14.
Figure 17:
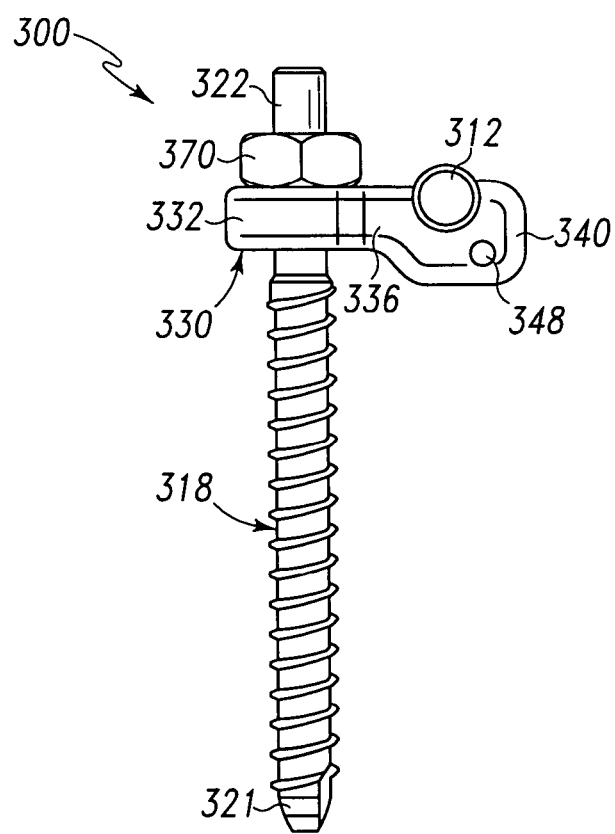
FIG. 17 is a side view of the spine fixation assembly of FIG. 14.
Figure 18:
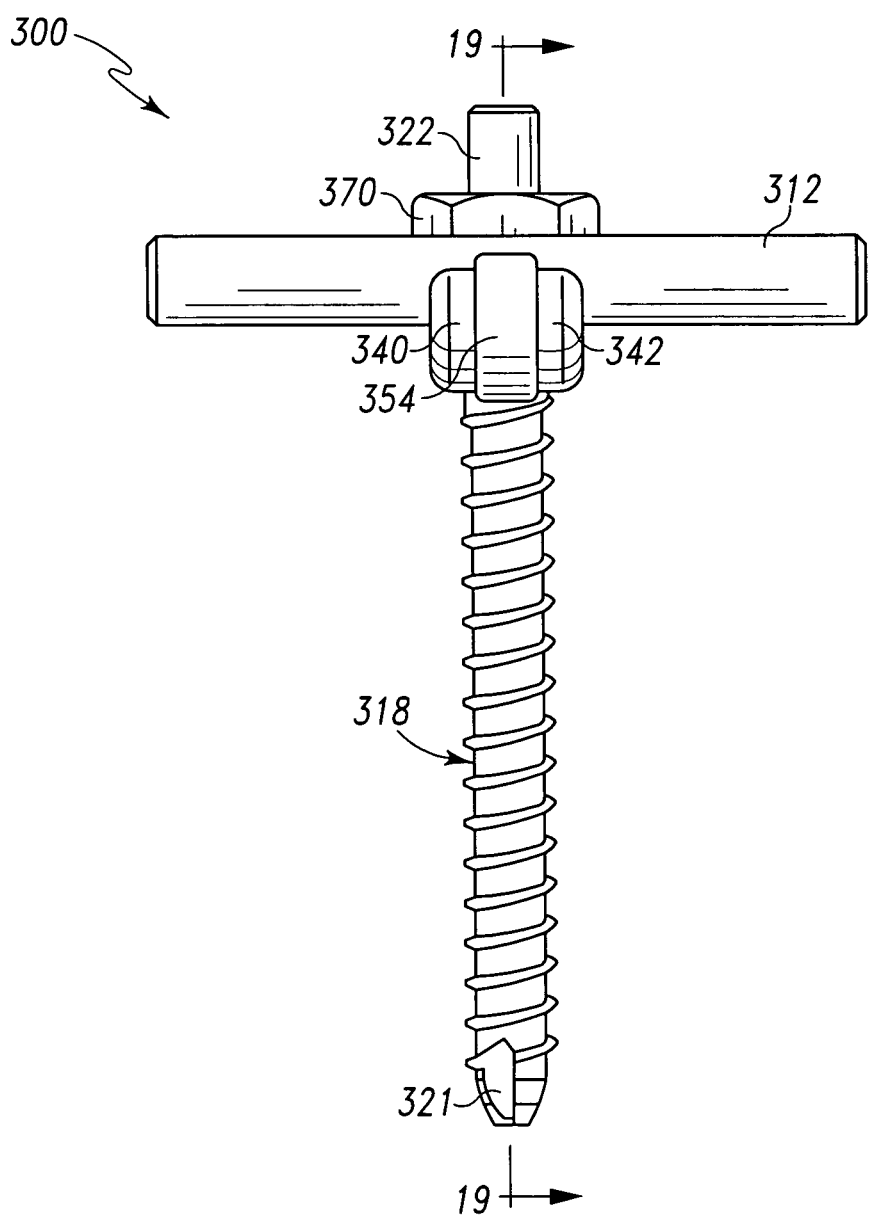
FIG. 18 is a front view of the spine fixation assembly of FIG. 14.
Figure 19:
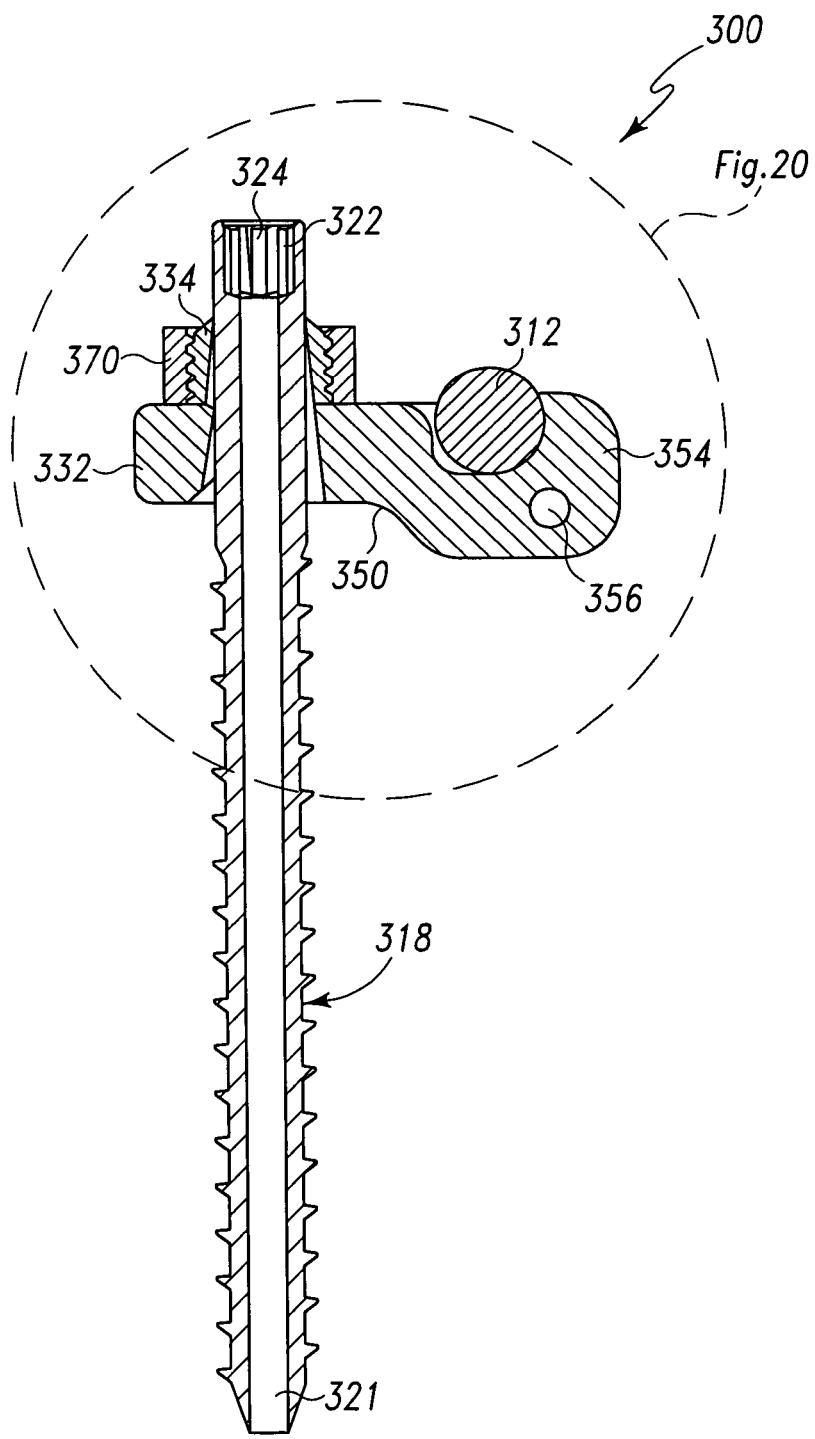
FIG. 19 is a sectional view of the spine fixation assembly of FIG. 14 taken along line 19-19 of FIG. 18.

The pawl 228 is defined by a body 250 having a generally annular portion 252 and a neck portion 256. The neck portion 252 has a bore 254 that is sized to be received about the upper portion 222 of the bone screw 202. The neck portion 256 also has a bore 258 for receipt of the pivot pin 248 therethrough. The neck portion 256 includes a flange 260 terminating in a pointed end, tip or lip 262. As best seen in FIG. 13, the lip 262 partially wraps around the spinal rod 212 when pivoted to aid in retaining the spinal rod in the connector 226 and provide an anti pop-out feature. The pawl body 250 is sized to be received in the channel 244 between the prongs 240 and 242. The pivot pin 248 is received through the bores in the connector 226 and the pawl 228 when assembled to allow the pawl 228 to pivot relative to the connector 226.

Figure 12:
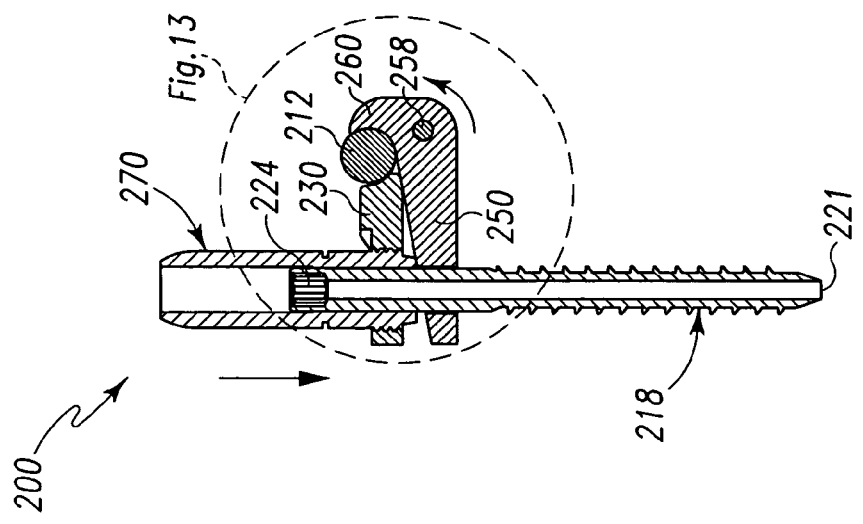
FIG. 12 is a sectional view of the spine fixation assembly of FIG. 9 taken along line 12-12 of FIG. 11.
Figure 11:
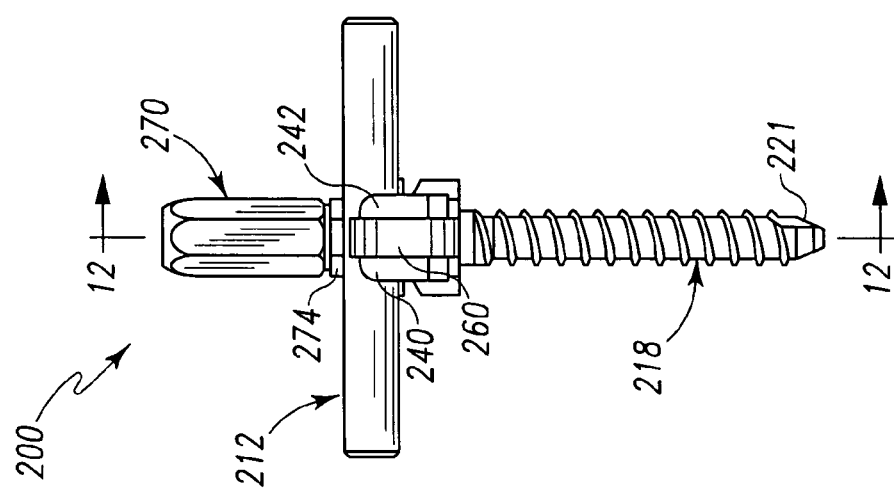
FIG. 11 is a front view of the spine fixation assembly of FIG. 9.
Figure 10:
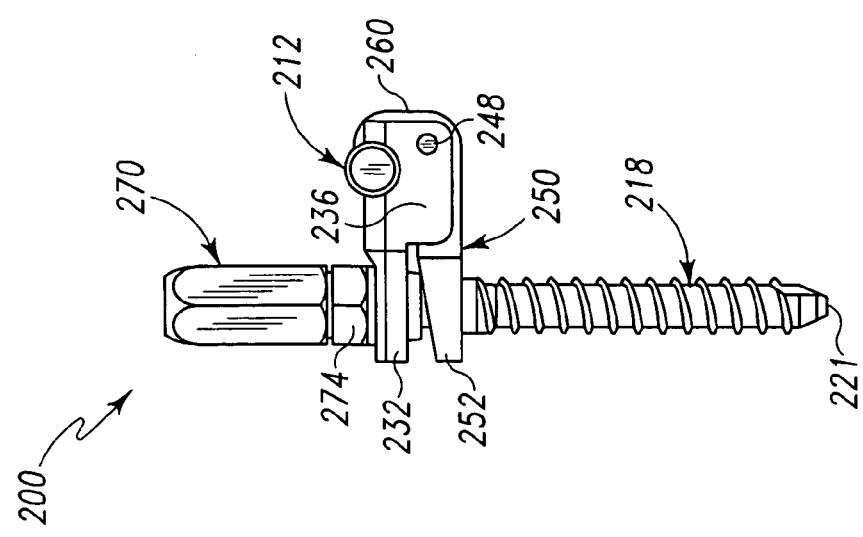
FIG. 10 is a side view of the spine fixation assembly of FIG. 9.

The fixation mechanism or nut 206 is defined by a body 270 formed by an upper portion 272, a middle portion 274, and a lower portion 278. As best seen in FIG. 12, the body 270 includes an internal bore that is sized to receive the upper portion 222 of the screw body 218. This allows the fixation mechanism 206 to be axially received onto the upper portion 222 of the bone screw body 218 and axially extend thereon as described herein. The middle portion 272 is configured as a hexagon to allow receipt of a hexagonal configured tool for threading the fixation mechanism 206 into the rod holder 204. The upper portion 272 is configured as an elongated hexagon to allow receipt of the hexagonal configured tool for threading the fixation mechanism 206 into the rod holder 204 as the middle portion 272 becomes inaccessible upon threading. The upper portion 272 and the middle portion 274 are joined at a break-away connection 276 to allow the upper portion 272 to be removed from the body 270 after being implanted. The lower portion 278 of the fixation mechanism is externally threaded for threaded reception into the threaded bore 234 of the connector 226 of the rod holder 204. The lower portion 278 also has a lower annular surface 280 that is configured to axially contact the upper surface of the annular portion 252 of the body 250 of the pawl 228 of the rod holder 204 as the fixation mechanism 206 is received by the connector 226 (see, e.g. FIG. 12).

The rod holder 204 of the spine fixation construct 200 locks onto the spinal rod 212 and is affixed to the bone screw 202 upon receipt of the fixation device 206 onto the bone screw 202 and in the rod holder 204. Particularly, as the fixation device 206 is threadedly received by the connector 230, the end 280 of the fixation device 206 abuts the upper surface of the pawl body 250. Since the pawl body 250 is pivotally connected to the connector body 230, the pawl body 250 pivots about the pivot pin 248 and thus the connector body 230 such that the inner surface 264 of the flange 260 holds the spinal rod 212 in the recess 238 of the connector body 230. The tip 262 of the flange 260 thus clamps about the spinal rod 212. Pivoting motion of the pawl body 250 by the fixation device 206 not only locks the spinal rod 212 but skews the pawl body 250 relative to the bone screw to wedge the pawl against the bone screw and fix the axial placement of the rod holder on the bone screw.

FIGS. 14-20 depict various views of another spine fixation construct 300 for holding a spinal rod portion 312 of a spinal rod (spinal rod) 310. The spine fixation construct 300 consists of a spinal rod holder or holding assembly 304, a bone screw 302, and a fixation mechanism 306. The spinal rod holder 304 is configured and/or adapted to be retained onto the bone screw 302 and to receive and retain the spinal rod portion 312 relative to the bone screw 302. The spinal rod holder 304 is further configured to lock onto the spinal rod portion 312. This locking of the spinal rod is accomplished upon receipt of the fixation mechanism 306 onto the bone screw 302. Particularly, as the fixation mechanism 306 is received onto the bone screw 302 the fixation mechanism 306 cooperates with the spinal rod holder 304 to cause the spinal rod holder 304 to lock onto the spinal rod 312. The spine fixation construct 300 provides locking of a spinal rod by the spinal rod holder 304 upon axial retention of the spinal rod holder 304 onto the bone screw 302 through cooperating action between the fixation mechanism 306 and the spinal rod holder 304.

The bone screw 302 is defined by a generally elongated cylindrical body or shaft 318 having a threaded lower portion or shank 320 tapering to an end or tip 321 and a smooth, generally cylindrical upper portion or head 322. The upper portion 322 has a configured socket 324 on the upper end thereof. The socket 324 is configured to allow receipt of a like-configured tool for threading the bone screw 318 into and out of a vertebral body, vertebrae or bone. The threaded lower portion 320 is configured to be received by the vertebral body, vertebrae or bone. The bone screw 302 is preferably, but not necessarily, configured as a pedicle screw.

The spinal rod holder or holding assembly 304 is defined by a connector 326, a rod retention or locking mechanism, latch, pawl or pivoting member 328, and a pivot pin 346. The pawl 328 is pivotally attached to the connector 326 through the pivot pin 346. The spinal rod holder 304 is configured to be received and fixed onto the bone screw 302 and particularly the upper portion 322 of the bone screw 302. The spinal rod holder 304 is further configured to receive the spinal rod 312 and lock or positively retain the spinal rod in cooperation with the fixation mechanism 306.

The connector 326 is defined by a body 330 having a generally annular portion 332, an externally threaded boss 334, a bore through the annular portion 332 and the boss 334, and a neck portion 336 essentially radially extending from the annular portion 332. The bore is sized to be received about the upper portion 322 of the bone screw 302. The neck portion 336 has first and second prongs or legs 340, 342 that define a slot or channel 344 therebetween. The neck portion 336 also has a rod reception area or recess 338 that is sized to receive the spinal rod 312. The first prong 340 has a bore 341 for receipt of the pivot pin 348 therethrough. The second prong 342 likewise has a bore (not seen) for receipt of the pivot pin 348 therethrough.

Figure 20:
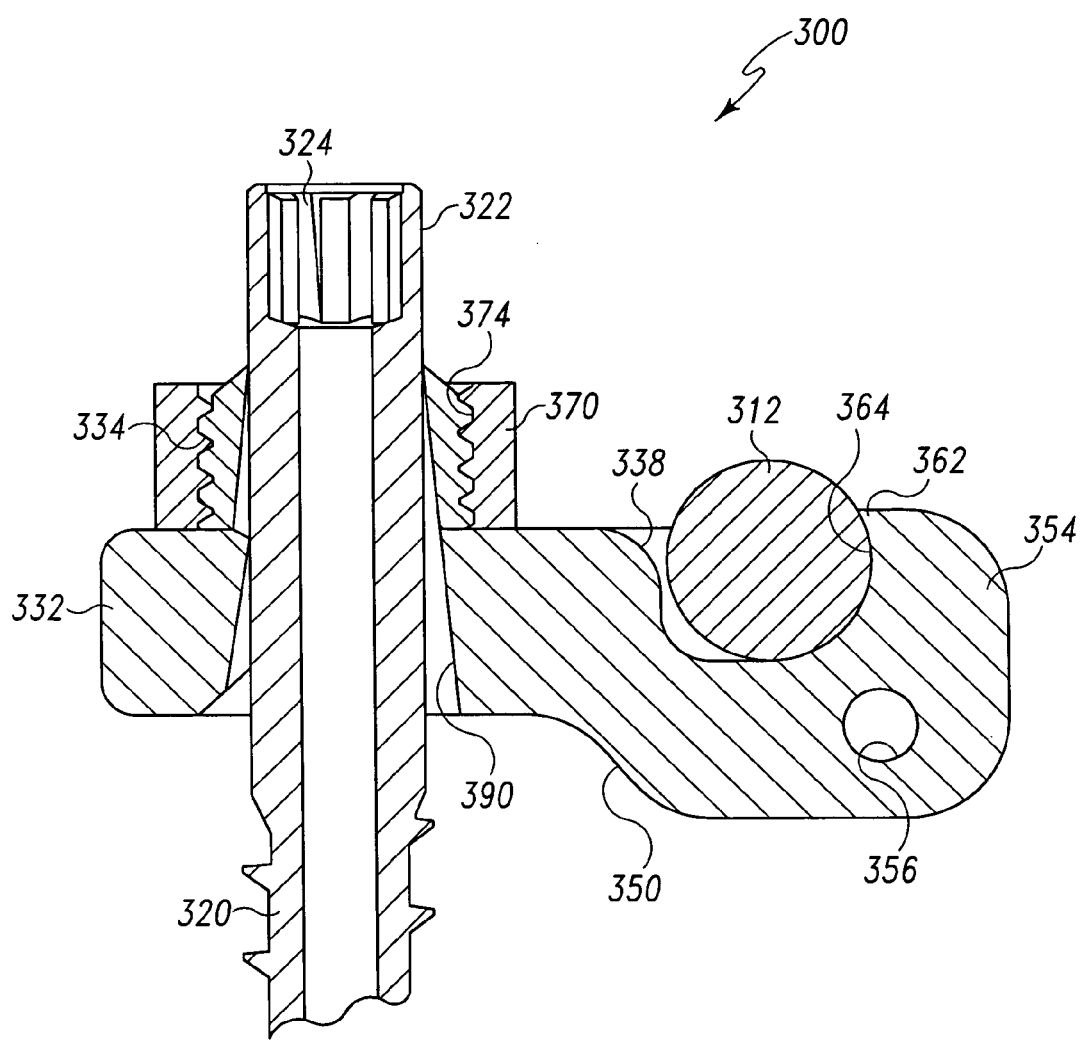
FIG. 20 is an enlarged view of a portion of the sectional view of FIG. 19 taken along circle 20-20 of FIG. 19.

The pawl 328 is defined by a generally flat body 350 sized to be received in the slot 344. The body 350 has a contact portion 352, a flange portion 354 and a spinal rod recess 358. A bore 356 is provided in the body 350 for receipt of the pivot pin 348 therethrough. The flange portion 354 terminates in a pointed end, tip or lip 362. As best seen in FIG. 20, the lip 362 partially wraps around the spinal rod 312 when pivoted to aid in retaining the spinal rod in the connector 326 and provide an anti pop-out feature. The pawl body 350 is sized to pivot in the channel 344 between the prongs 340 and 342. The pivot pin 348 is received through the bores in the connector 326 and the pawl 328 when assembled to allow the pawl 328 to pivot relative to the connector 326.

The fixation mechanism or nut 306 is defined by a body 370 having a hexagonal outer surface 372. The body 370 includes an internally threaded bore 374 that is sized to be threadedly received on the threaded boss 334.

The rod holder 304 of the spine fixation construct 300 locks onto the spinal rod 312 and is affixed to the bone screw 302 upon receipt of the fixation device 306 onto the boss 334 of the rod holder 304. Particularly, as the fixation device 306 is threadedly received by the boss 334 (connector 330), the body 370 abuts the contact portion 352 of the pawl body 350. Since the pawl body 350 is pivotally connected to the connector body 330, the pawl body 350 pivots about the pivot pin 348 and thus the connector body 330 such that the inner surface 364 of the flange 354 holds the spinal rod 312 in the recess 338 of the connector body 330. The tip 362 of the flange 354 thus clamps about the spinal rod 312. Pivoting motion of the pawl body 350 by the nut 306 not only locks the spinal rod 312 but skews the pawl body 350 relative to the bone screw to wedge the pawl against the bone screw and fix the axial placement of the rod holder on the bone screw. As best seen in FIG. 20, the bore of the connector body 350 includes a taper 390. The taper allows for slight angulation.

The various components of the present spine fixation constructs 10, 200 and 300 are made from a bio-compatible material such as stainless steel or titanium. Other bio-compatible materials, or course, may be used.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A spine fixation construct for receiving and retaining a spinal rod onto a bone screw, the spine fixation construct comprising:
    a rod holder configured to be axially received and positioned onto the bone screw and to receive and lock onto a spinal rod when engaged, the rod holder comprising:
        a connector having a pair of spaced apart prongs to receive the spinal rod and define a slot therebetween;
        a pawl at least partially disposed in the slot between the prongs and pivotally coupled to the connector to pivot within the slot between the prongs;
    a fixation component configured to be axially received on the bone screw and the rod holder,
    wherein engagement of the rod holder by the fixation component pivots the pawl into an engagement with both the spinal rod and the bone screw;
    wherein the connector comprises an annular bore to axially receive the bone screw;
    wherein the pawl is pivotally attached to the connector via a pivot pin extending between the prongs and parallel to the spinal rod; and
    wherein the fixation component threadably engages the annular bore in the connector.

2. The spine fixation construct of claim 1, wherein the pawl defines a contact surface that is abutted by the fixation component to cause pivoting of the pawl.

3. The spine fixation construct of claim 2, wherein the pawl defines a lip that at least partially wraps around the spinal rod when the rod holder is engaged by the fixation component.

4. The spine fixation construct of claim 1, wherein the pawl defines a lip that at least partially wraps around the spinal rod when the rod holder is engaged by the fixation component.

5. The spine fixation construct of claim 4, wherein both the prongs and the lip of the pawl extend upwardly.

6. A spine fixation construct for receiving and retaining a spinal rod, the spine fixation construct comprising: a bone screw having a threaded shank and a head, and defining a longitudinal axis;
 a fixation nut; and
 a rod holder assembly configured to be axially adjustably received onto the bone screw, the rod holder assembly having a connector and a pivot member configured to pivot relative to the connector and the spinal rod, the pivot member having a concave inner surface that contacts and at least partially wraps around the spinal rod;
 wherein the fixation nut threadably engages an annular first bore in the connector and engages the pivot member to pivot the pivot member to engage and lock the spinal rod relative to the connector and engage and lock the bone screw relative to the connector.

7. The spine fixation construct of claim 6, wherein the connector includes a spinal rod retention area for receiving the spinal rod and a channel in communication with the spinal rod retention area; and
 wherein the pivot member is disposed in the channel and pivotally attached to the connector to abut and lock onto the spinal rod in the spinal rod retention area when pivoted by the fixation nut as the fixation nut engages the rod holder assembly.

8. The spine fixation construct of claim 7, wherein the pivot member comprises a body and an upwardly extending flange, the upwardly extending flange configured to at least partially wrap around the spinal rod.

9. The spine fixation construct of claim 8, wherein the pivot member defines a second bore that receives the bone screw, and wherein pivoting of the pivot member causes the second bore to engage and lock the bone screw relative to the connector.

10. The spine fixation construct of claim 6, wherein the connector includes an annular bore for reception by the bone screw and a pair of spaced apart prongs, the pair of spaced apart prongs defining a spinal rod retention area for receiving the spinal rod and a slot in communication with the spinal rod retention area; and
 wherein the pivot member is disposed in the slot and pivotally attached to the connector via a pivot pin extending through the prongs and the pivot member, the pivot member is configured to abut and lock onto the spinal rod in the spinal rod retention area when pivoted by the fixation nut as the fixation nut engages the rod holder assembly.

11. The spine fixation construct of claim 10, wherein the pivot member defines a contact surface that is abutted by the fixation nut to cause pivoting of the pivot member.

12. The spine fixation construct of claim 11, wherein the pivot member defines a lip that surrounds the spinal rod when the rod holder assembly is engaged by the fixation nut.

13. A spine fixation construct comprising:
 a bone screw having a threaded shank and a head, and defining a longitudinal axis;
 a rod holder configured to be axially received and positioned onto the head of the bone screw and to receive and lock onto a spinal rod, the rod holder having a connector and a pawl coupled to the connector by a pivot pin, the pivot pin generally perpendicular to the longitudinal axis; and
 a fixation device configured to be both axially received on the head of the bone screw and by the connector, the fixation device further configured to pivot the pawl to lock the spinal rod relative to the rod holder;
 wherein the fixation device threadably engages an annular bore in the connector.

14. The spine fixation construct of claim 13, wherein the connector includes a spinal rod retention area for receiving the spinal rod and a channel in communication with the spinal rod retention area; and
 a pawl disposed in the channel and pivotally attached to the connector, the pawl configured to abut and lock onto the spinal rod in the spinal rod retention area when pivoted by the fixation device as the fixation device engages the rod holder.

15. The spine fixation construct of claim 14, wherein the pawl defines a contact surface that is abutted by the fixation device to cause pivoting of the pawl.

16. The spine fixation construct of claim 15, wherein the pawl defines a lip that surrounds the spinal rod when the rod holder is engaged by the fixation device.

17. The spine fixation construct of claim 14, wherein the pawl includes a first portion that directly engages the spinal rod and a second portion separate from the first portion that directly engages the bone screw.

18. The spine fixation construct of claim 17, wherein the first portion comprises a curved contact surface that at least partially wraps around the spinal rod.

19. The spine fixation construct of claim 18, wherein the second portion comprises a bore to axially receive the bone screw.

20. The spine fixation construct of claim 13, wherein the connector includes a pair of spaced apart prongs and an annular bore for reception by the bone screw, the pair of spaced apart prongs defining a spinal rod retention area for receiving the spinal rod and a slot in communication with the spinal rod retention area; and
 wherein the pivot pin extends through the pawl between the two spaced apart prongs.

21. The spine fixation construct of claim 20, wherein the pawl defines a contact surface that is abutted by the fixation device to cause pivoting of the pawl.

* * * * *